(12) United States Patent
Mayenberger et al.

(10) Patent No.: US 8,105,348 B2
(45) Date of Patent: Jan. 31, 2012

(54) SURGICAL OBTURATOR

(75) Inventors: Rupert Mayenberger, Rielasingen (DE); Johann Maliglowka, Kolbingen (DE)

(73) Assignee: Aesculap AG, Tuttlingen (DE)

( * ) Notice: Subject to any disclaimer, the term of this patent is extended or adjusted under 35 U.S.C. 154(b) by 345 days.

(21) Appl. No.: 12/455,680

(22) Filed: Jun. 3, 2009

(65) Prior Publication Data
US 2009/0306698 A1 Dec. 10, 2009

Related U.S. Application Data

(63) Continuation of application No. PCT/EP2007/009299, filed on Oct. 26, 2007.

(30) Foreign Application Priority Data

Dec. 14, 2006 (DE) .......................... 10 2006 059 012

(51) Int. Cl.
*A61B 17/34* (2006.01)
(52) U.S. Cl. ....................................... 606/185; 606/172
(58) Field of Classification Search .................. 606/184, 606/185, 172, 108; 604/110, 111, 158, 164.01, 604/164.08, 164.12, 167.01, 162, 192; 27/21.1; 401/109–112
See application file for complete search history.

(56) References Cited

U.S. PATENT DOCUMENTS

| | | | |
|---|---|---|---|
| 3,051,132 A * | 8/1962 | Johmann | 401/103 |
| 5,066,288 A | 11/1991 | Deniega et al. | |
| 5,215,526 A * | 6/1993 | Deniega et al. | 604/164.09 |
| 5,324,268 A | 6/1994 | Yoon | |
| 5,342,382 A | 8/1994 | Brinkerhoff et al. | |
| 5,346,459 A | 9/1994 | Allen | |
| 5,360,405 A * | 11/1994 | Yoon | 604/164.12 |
| 5,423,770 A | 6/1995 | Yoon | |
| 5,462,532 A | 10/1995 | Gresl | |
| 5,569,289 A | 10/1996 | Yoon | |
| 5,591,191 A | 1/1997 | Kieturakis | |
| 5,609,604 A | 3/1997 | Schwemberger et al. | |
| 5,645,076 A | 7/1997 | Yoon | |
| 5,662,673 A | 9/1997 | Kieturakis | |
| 5,674,237 A * | 10/1997 | Ott | 606/185 |
| 5,676,156 A | 10/1997 | Yoon | |
| 5,755,697 A | 5/1998 | Jones et al. | |
| 5,779,680 A | 7/1998 | Yoon | |
| 5,807,402 A | 9/1998 | Yoon | |

(Continued)

FOREIGN PATENT DOCUMENTS

DE 44 11 685 10/1995

(Continued)

*Primary Examiner* — Kathleen Sonnett
*Assistant Examiner* — Rachel S Papeika
(74) *Attorney, Agent, or Firm* — Lipsitz & McAllister, LLC

(57) ABSTRACT

A surgical obturator is provided which has a tubular housing, a blade carrier displaceable in the tubular housing in a longitudinal direction between an advanced cutting position and a retracted protected position. A blade with a cutting edge is held on the blade carrier. A protective cap engages over the blade and is displaceable in the tubular housing in the longitudinal direction between an advanced rest position in which the blade is completely covered in its protected position and a retracted work position. The protective cap has a slit through which the cutting edge passes. In a work position of the protective cap, the blade projects through the slit. A retracting device is arranged in the tubular housing for displacing the blade from the cutting position to the protected position. The retracting device is activatable by displacement of the protective cap from the work position to the rest position.

19 Claims, 14 Drawing Sheets

U.S. PATENT DOCUMENTS

| | | |
|---|---|---|
| 2003/0100914 A1 | 5/2003 | O'Heeron et al. |
| 2009/0138034 A1 | 5/2009 | Maliglowka et al. |

FOREIGN PATENT DOCUMENTS

| | | |
|---|---|---|
| DE | 197 18 086 | 11/1998 |
| DE | 20 2006 008 405 | 7/2006 |
| DE | 20 2006 008 406 | 7/2006 |
| DE | 202006008405 U1 * | 8/2006 |
| DE | 20 2006 018 883 | 2/2007 |
| EP | 0 135 364 | 3/1985 |
| EP | 0 495 633 | 7/1992 |
| EP | 0 499 457 | 8/1992 |
| EP | 0 551 968 | 7/1993 |
| EP | 0 600 921 | 6/1994 |
| EP | 0 705 077 | 4/1996 |
| WO | 89/03661 | 5/1989 |

* cited by examiner

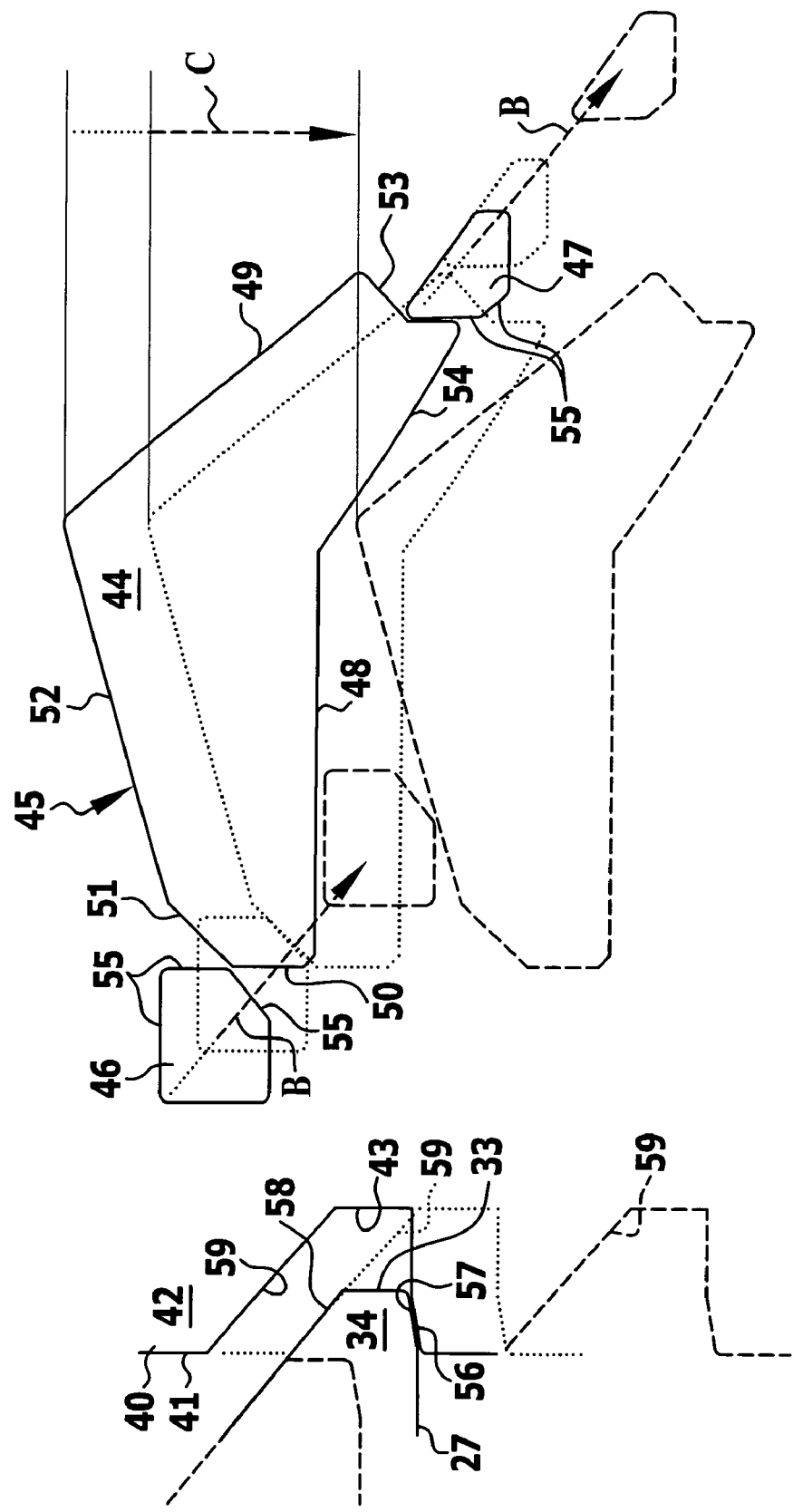

SURGICAL OBTURATOR

This application is a continuation of international application number PCT/EP2007/009299 filed on Oct. 26, 2007.

The present disclosure relates to the subject matter disclosed in international application number PCT/EP2007/009299 of Oct. 26, 2007 and German application number 10 2006 059 012.0 of Dec. 14, 2006, which are incorporated herein by reference in their entirety and for all purposes.

BACKGROUND OF THE INVENTION

The invention relates to a surgical obturator for piercing a body wall with a tubular housing, with a blade carrier displaceable in the tubular housing in the longitudinal direction between an advanced cutting position and a retracted protected position, a blade with a cutting edge being held on the blade carrier, the cutting edge being guided in a correspondingly extending guide of the tubular housing, with a protective cap engaging over the blade and being displaceable in the tubular housing in the longitudinal direction between an advanced rest position in which the blade is completely covered in its protected position and a retracted work position, the protective cap having a slit through which the cutting edge of the blade passes and, in the work position of the protective cap, projects over the latter, and with a retracting device arranged in the tubular housing and displacing the blade from the cutting position to the protected position, the retracting device being activatable by displacement of the protective cap from the work position to the rest position.

Such a surgical obturator is described in German utility model 20 2006 008 405 U1. Herein the retracting device is arranged in the grip area of the obturator where quite a lot of space is available for complex mechanics of the retracting device.

Such retracting devices are also known from other known surgical obturators. These ensure that the blade or a trocar tip is automatically retracted when the body wall is fully pierced. In all cases, the constructions of the retracting devices are complicated. These retracting devices have a lot of parts and a large space requirement and, therefore, in all cases, they must be arranged in an area remote from the blade or the trocar tip, in some cases, in the grip of the obturator (EP 0 499 457 B1; EP 0 705 077 B1; EP 0 600 921 B1) or in an unwieldy special construction (U.S. Pat. No. 5,462,532 A).

The object of the invention is to so construct a generic surgical obturator that the retracting device is of less complicated construction and has a lower space requirement than known retracting devices.

SUMMARY OF THE INVENTION

This object is accomplished in a surgical obturator of the kind described at the outset, in accordance with the invention, in that the retracting device comprises a switching element which fixes the blade in the cutting position and, upon activation, releases the blade for displacement to the rest position, the switching element being mounted in the tubular housing so as to be freely rotatable about the longitudinal axis of the tubular housing and immovable in the longitudinal direction, and the switching element being rotatable for switchover, upon displacement of the blade carrier and/or the protective cap in the longitudinal direction of the tubular housing, by means of a cam guide which is operative between the switching element, on the one hand, and the blade carrier and/or the protective cap, on the other hand.

The movements of the protective cap and the blade carrier, which essentially take place in the longitudinal direction of the tubular housing, are thus used to rotate a switching element by means of cam guides about the longitudinal axis of the tubular housing. This rotational movement of the switching element is used to fix the blade carrier in the cutting position and release it again once the protective cap, after penetration of the body wall, is displaced from the work position to the rest position. The conversion of the displacement of the blade carrier and the protective cap to a rotational movement of the switching element enables a compact construction with only a few individual parts to be achieved and, therefore, this retracting mechanism can be accommodated in the tubular housing itself, preferably in the immediate area of the blade carrier. This does not require the outer dimensions of the tubular housing to be increased or special accommodation areas to be provided for the retracting device.

In accordance with a preferred embodiment, the protective cap is acted upon by a spring which displaces the protective cap from the work position to the rest position. The displacement of the protective cap to the work position thus takes place against the force of this spring. This spring is also responsible for the protective cap, following complete penetration of the body wall, no longer being held back by the body wall, but being displaced by the opening created by the obturator into the rest position.

Furthermore, it may be provided that the blade carrier is acted upon by a spring which displaces the blade carrier from the cutting position to the protected position. This spring is responsible for the blade carrier, following completion of the cutting operation and by virtue of the displacement of the protective cap from the work position to the rest position, which activates the retracting device, being retracted from the cutting position to the protected position.

Provision is made in accordance with a particularly preferred embodiment for the protective cap and the blade carrier to be acted upon by a common spring which pushes these apart, the common spring displacing, on the one hand, the protective cap from the work position to the rest position and, on the other hand, the blade carrier from the cutting position to the protected position. In this construction, this spring is accorded a double function.

Here it is particularly advantageous for the spring to be a helical spring which is arranged in the interior of the blade carrier and is supported on a projection of the protective cap that extends through the wall of the blade carrier into the interior thereof. In this way, a very compact arrangement of protective cap, blade carrier and spring is obtained.

The cutting edge of the blade may be straight-lined. However, in accordance with a preferred embodiment, provision is made for the cutting edge of the blade to be of helical configuration, so that the blade carrier, upon displacement in the longitudinal direction relative to the tubular housing, and the protective cap upon longitudinal displacement relative to the blade carrier, are rotated relative to each other about the longitudinal axis of the blade carrier. This rotation takes place by virtue of the guidance of the cutting edge in the tubular housing and by virtue of the guidance of the protective cap imparted to it by the cutting edge passing through the slit in the protective cap. A helical guidance of the cutting edge has the advantage that when piercing the body wall, the surgeon can perform this in a particularly sensitive manner with a combined advancing and rotational movement. This construction also has the advantage that the component of the rotational movement imparted to the blade carrier and the protective cap can also contribute to the rotation of the switching element.

The blade carrier may advantageously comprise a sleeve-shaped shaft which is arranged concentrically with the tubular housing.

It is expedient for the blade carrier to be connected to a push rod which extends through the tubular housing as far as a push device at the end of the tubular housing remote from the blade. By means of this push rod which, for example, may be provided with a pushbutton, the blade carrier can be displaced forwards in the longitudinal direction in the tubular housing, so that the blade carrier can thereby move from the retracted protected position to the advanced cutting position.

Provision is made in accordance with a particularly preferred embodiment for the switching element to be a sleeve which concentrically surrounds the blade carrier. This concentric arrangement allows accommodation of the parts in an extremely small space and also enables optimal functioning of the cam guide operative between blade carrier and switching element.

It may then be provided that the cam guide operative between the switching element and the blade carrier is formed by cam tracks and cams adapted to abut thereon, the cams and the cam tracks being arranged on the outer side of the blade carrier and on the inner wall of the sleeve-shaped switching element, respectively.

In particular, it is advantageous for a plurality of similar cam tracks and cams to be arranged along the circumference of the blade carrier and the sleeve-shaped switching element such that in successive work cycles the cams respectively abut on an adjacent cam track. Thus, in one work cycle the switching element is switched further through a certain angular amount, and after such a work cycle the cams then abut on the following, identically constructed cam track. A work cycle is characterized by the blade carrier being displaced from its retracted protected position to the advanced cutting position, blocked there and, following complete piercing of the body wall, released again by displacement of the protective cap from the work position to the rest position and pushed back into its retracted protected position, so that the assembly again reaches its initial state.

Provision is made in a particularly preferred embodiment for each cam track to have associated with it two cams which, upon displacement of the blade carrier relative to the switching element, abut one after the other on the cam track. During the displacement of the blade carrier, these cams bring about one after the other a rotation of the switching element.

The cam track can be formed by the edge of an island-shaped projection along which the cams slide in a work cycle and thereby bring about a rotational movement of the switching element.

Provision is made in a particularly preferred embodiment for a first or front cam facing the blade, upon displacement of the blade carrier from the protected position in the direction towards the cutting position, to slide along a first section of the cam track that extends at an incline to the direction of displacement of the blade carrier and to thereby rotate the switching element from an initial position in a first direction, for a second or rear cam facing away from the blade to enter into abutment with a second section of the cam track that extends in the opposite direction at an incline to the direction of displacement of the blade carrier once the front cam has moved past the first section of the cam track, so that the switching element is rotated in the opposite direction into a blocking position in which, upon subsequent retraction of the blade carrier from an end position located in front of the cutting position, a stop arranged on the blade carrier strikes a stop on the switching element and thereby prevents any further retraction of the blade carrier. In this arrangement the blade carrier is therefore not only advanced out of the retracted protected position into the advanced cutting position, but beyond that. This further displacement beyond the cutting position serves to rotate the switching element into a blocking position, so that upon retraction of the blade carrier in the direction towards the cutting position, a further rearward movement of the blade carrier is blocked by the stops, i.e. the blade remains in an advanced position.

It is expedient for the stop on the blade carrier to be formed by the front cam. There is then no need for a separate stop, which further simplifies the construction.

The stop on the switching element can be formed by a third section of the cam track that extends transversely to the longitudinal direction of the tubular housing. This also contributes towards simplification of the construction.

Furthermore, it may be provided that the cam track and the cams between the switching element and the protective cap are formed by the side flanks of teeth which are arranged on the end faces of the protective cap and the switching element that face one another, and which are in engagement when the protective cap is retracted into the work position. Both the protective cap and the switching element thus carry at their end faces that face one another teeth which are not in engagement so long as the protective cap is in its advanced rest position, but which engage once the protective cap is retracted into the work position.

The flanks of the teeth can be so arranged and designed that the teeth of the protective cap, upon retraction of the protective cap from the rest position to the work position, rotate the switching element from its blocking position in the first direction until the stop of the blade carrier reaches a fourth section of the cam track of the switching element, which extends at an incline to the longitudinal direction of the tubular housing and adjoins the stop of the switching element. Once the stop of the blade carrier abuts on this fourth section, the blade carrier, under the action of the spring acting upon it, exerts a force on the switching element and attempts to rotate it in the second direction.

However, in accordance with a further preferred embodiment, such a rotation is prevented by the flanks of the teeth being so designed that a rotation of the switching element in the second direction under the influence of the stop of the blade carrier abutting on the fourth section being limited such that the blade carrier, in relation to its position with the two stops abutting on each other, is retracted only slightly as far as its cutting position. The blade carrier is therefore blocked in a cutting position which is retracted only slightly in relation to the blocked position. In this cutting position, the piercing of the body wall can take place as the blade carrier is prevented by the switching element from retracting in the direction towards the protected position.

Furthermore, it may be provided that the engagement of the teeth of the blade carrier and the protective cap is released upon displacement of the protective cap into the rest position, so that the limitation of the rotatability of the switching element is eliminated. Once this occurs, the blade carrier can be retracted under the influence of the spring into the protected position, i.e., the displacement of the protective cap to the rest position triggers the rearward movement of the blade carrier.

It is advantageous for the cam track to have a fifth section which adjoins the inclined fourth section and along which the front cam of the blade carrier slides upon retraction of the blade carrier from the cutting position to the protected position and thereby rotates the switching element in the second direction into the initial position for the next work cycle.

In accordance with a further preferred embodiment, when the switching element is located in the blocking position and the stop of the blade carrier is in abutment with the fourth section of the cam track, the rear cam of the blade carrier is located opposite a sixth section of the cam track, which prevents a displacement of the blade carrier in the direction from the protected position to the cutting position. In its location in the cutting position, the blade is therefore fixed in both directions, and it is not possible for the blade to be inadvertently advanced beyond the cutting position by actuation of the push rod.

The following description of preferred embodiments of the invention serves in conjunction with the drawings for further explanation.

BRIEF DESCRIPTION OF THE DRAWINGS

FIG. 14 a view, similar to FIG. 13, during the displacement of the blade carrier into the cutting position and subsequently from the cutting position back into the protected position and therefore into the initial position of the switching element.

DETAILED DESCRIPTION OF THE INVENTION

Figure 1:
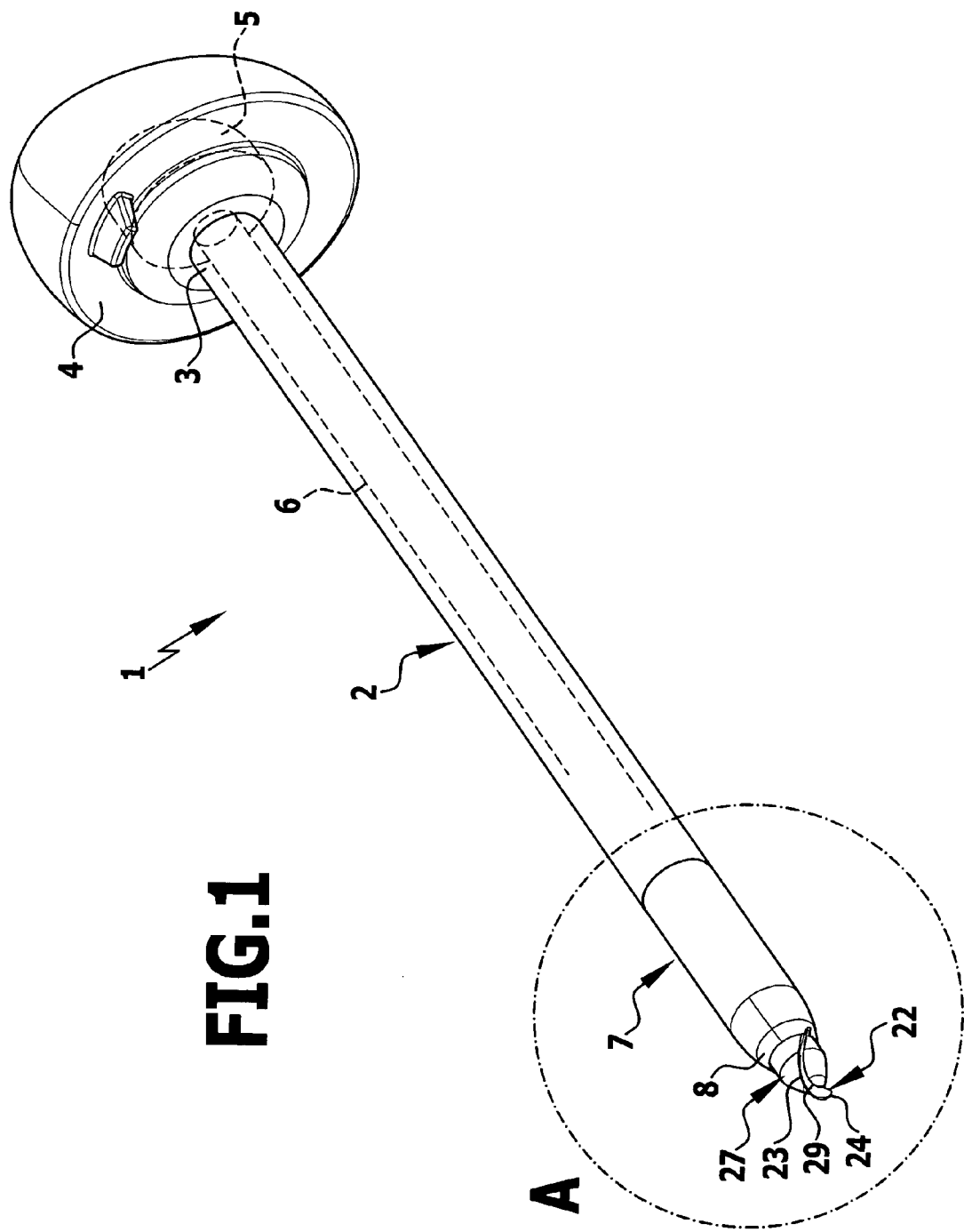
FIG. 1 a perspective view of a surgical obturator with a tubular housing and a blade with a helical cutting edge.
Figure 2:
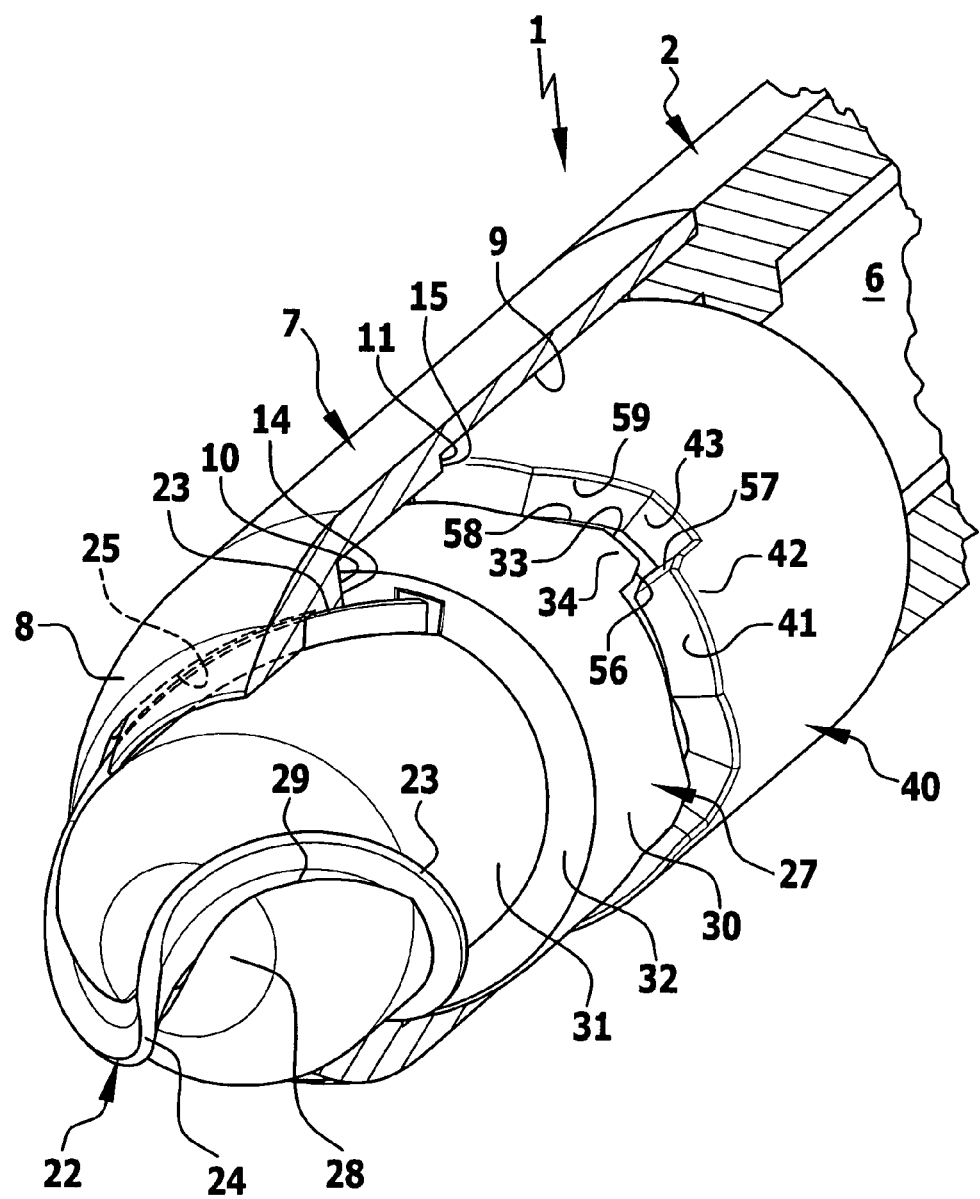
FIG. 2 an enlarged detail view of area A in FIG. 1 with the tubular housing cut in the longitudinal direction.
Figure 3:
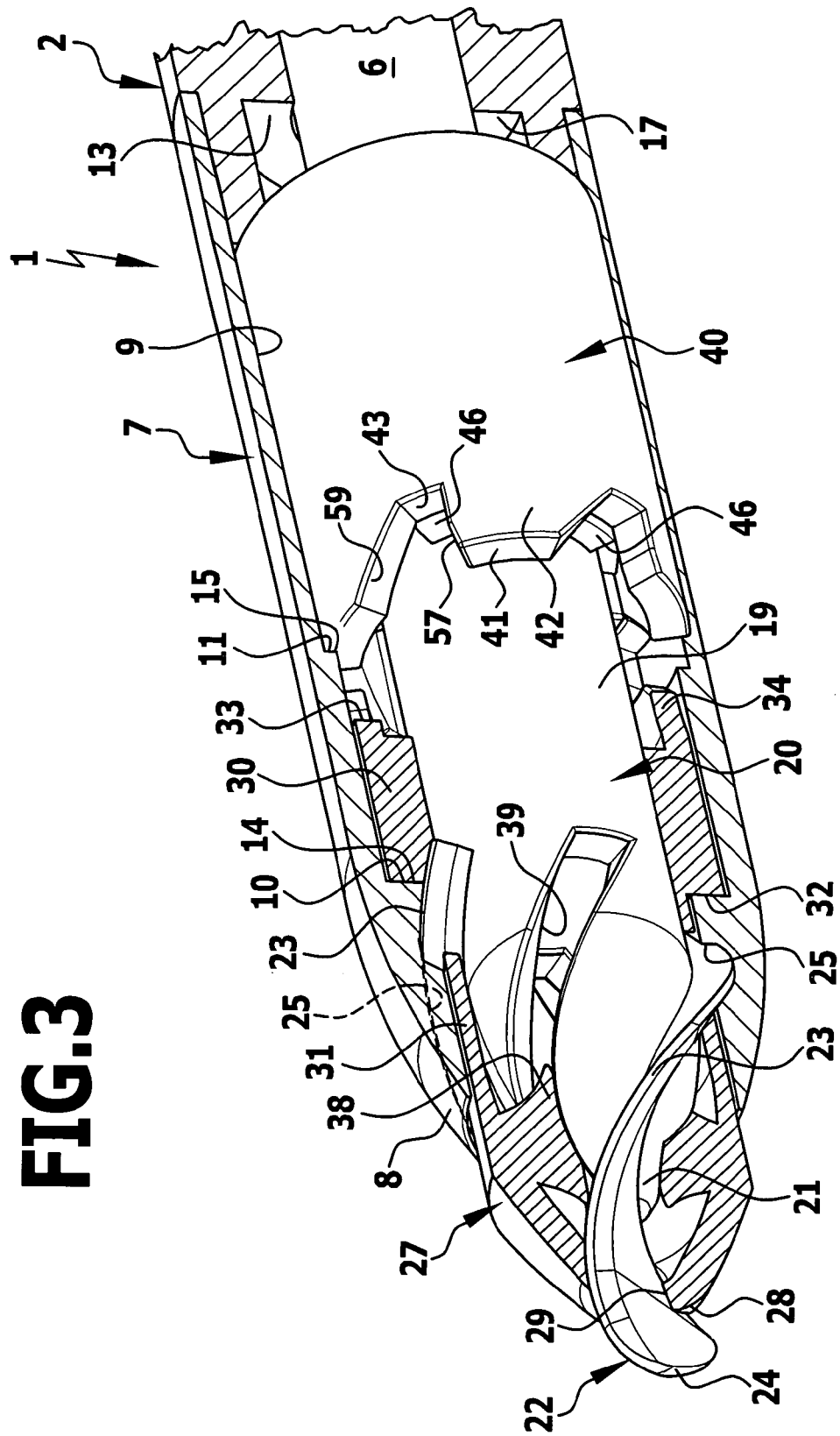
FIG. 3 a view, similar to FIG. 2, in which, in addition, the protective cap is cut in the longitudinal direction.
Figure 4:
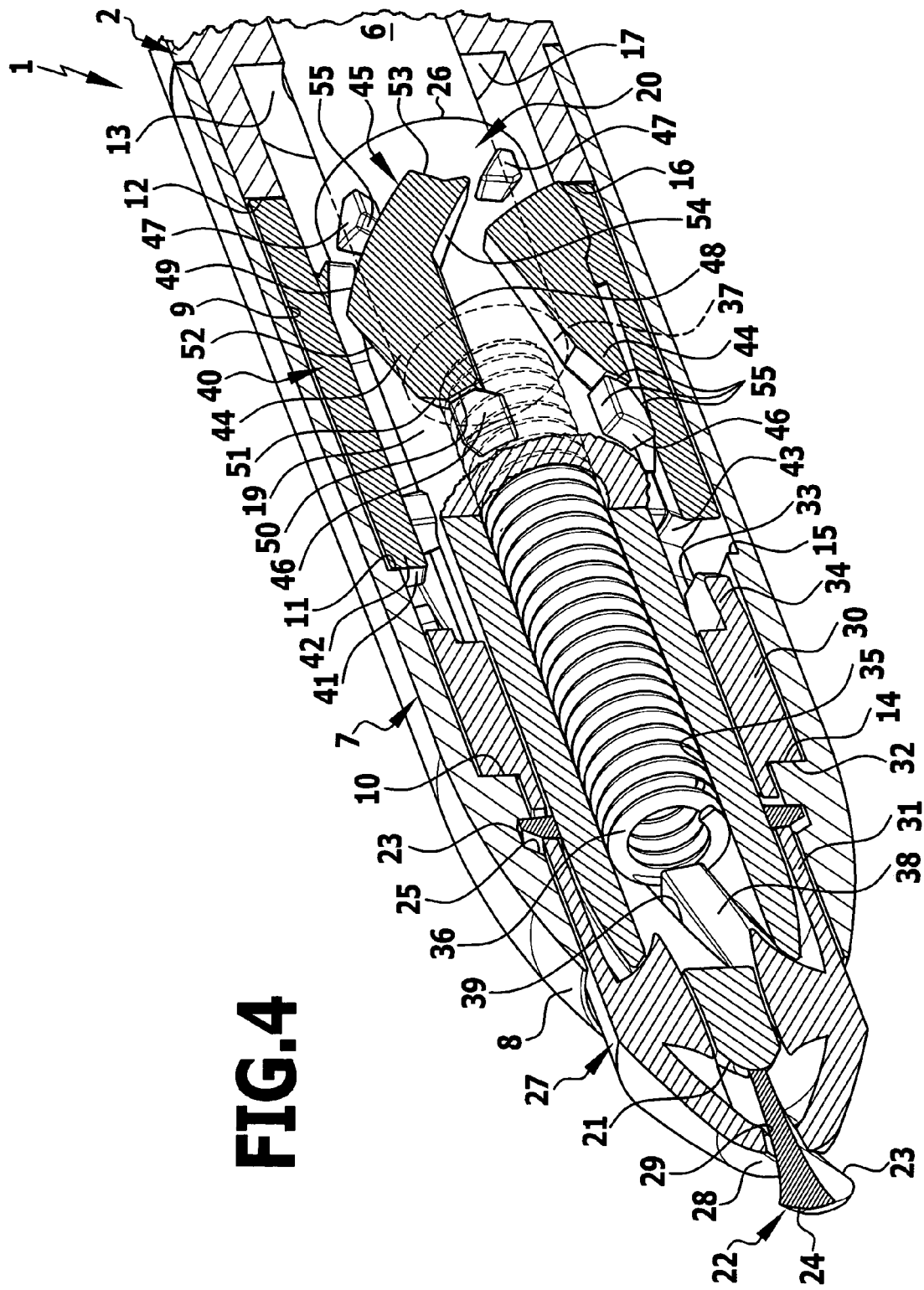
FIG. 4 a view, similar to FIG. 3, in which, in addition, the switching element and partially the blade carrier are cut in the longitudinal direction.

The surgical obturator 1 shown in the drawings comprises an elongated, tubular housing 2, at the rear end 3 of which a grip 4 of enlarged diameter is arranged. A pushbutton 5 is mounted in the grip 4 for displacement in the longitudinal direction of the housing 2. The pushbutton 5 is actuatable from the rear side of the grip 4 and is connected to a push rod 6 which leads in the interior of the tubular housing 2 to the front area A thereof.

In this front area A, the tubular housing 2 ends in a substantially circular cylindrical end cap 7 forming part of the tubular housing 2 and tapering towards its front end 8. The end cap 7 is open at its front end 8.

Figure 6:
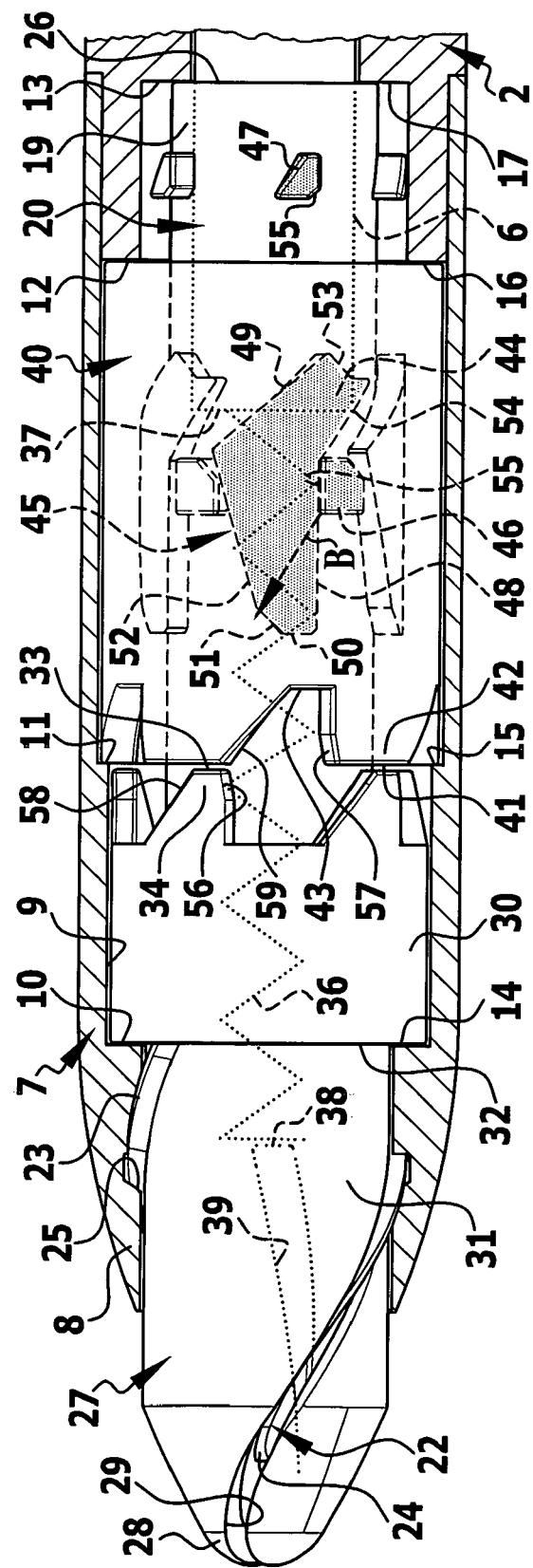
FIG. 6 a longitudinal sectional view of the obturator of FIG. 1 in the initial position with advanced protective cap and retracted blade carrier.
Figure 7:
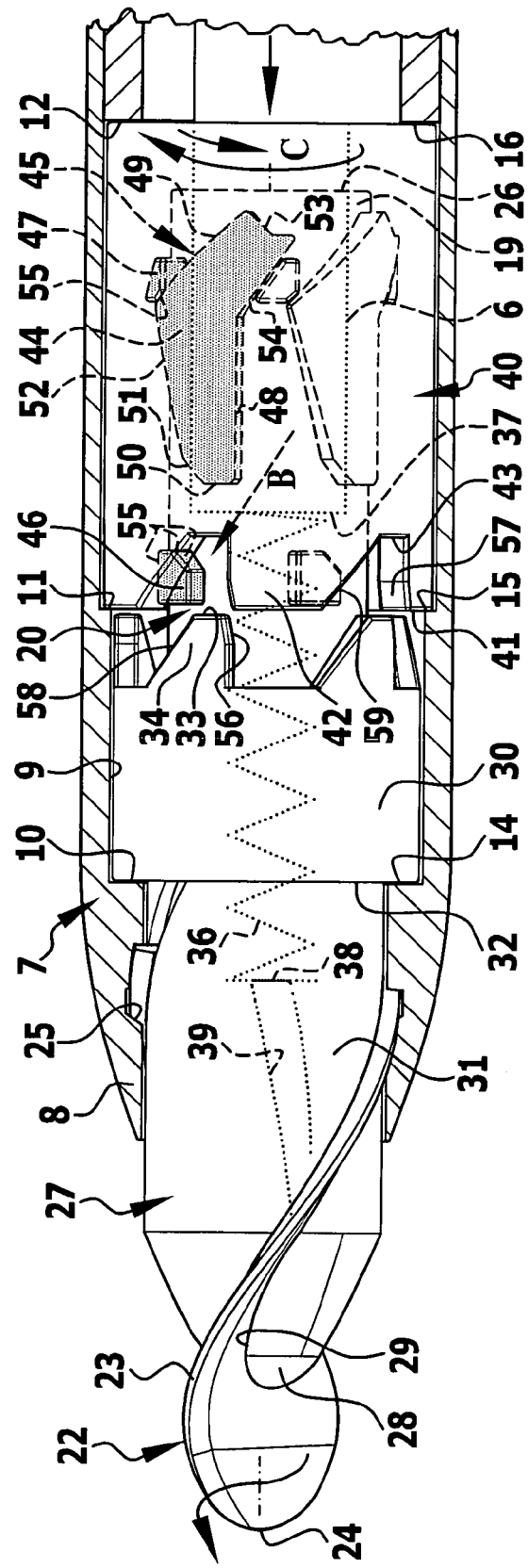
FIG. 7 a view, similar to FIG. 6, with the blade carrier advanced forwards over the cutting position.

The end cap 7 encloses an interior 9 which, starting from the front end 8, comprises two successive step-shaped widenings 10, 11 and then two successive step-shaped narrowings 12, 13, so that ring shoulder-shaped projections 14, 15, 16, 17 are respectively formed at these step-shaped widenings and narrowings (FIG. 6).

Figure 5:
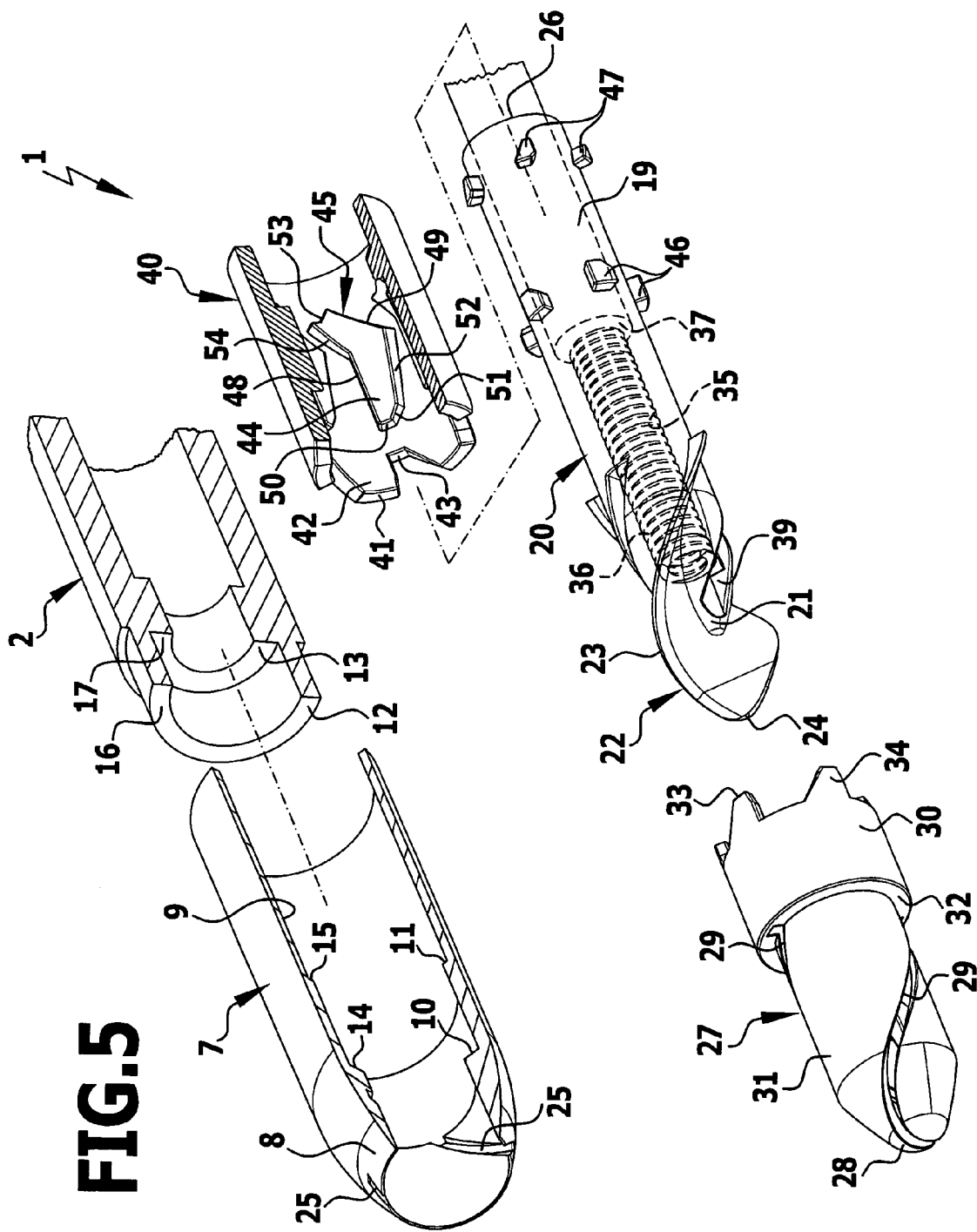
FIG. 5 an exploded representation of the front part of the tubular housing, the blade carrier, the protective cap and the switching element.

The push rod 6 is fixedly connected to a cylindrical shaft 19 of a blade carrier 20 which extends through the entire interior 9 and at its front end 21 carries a blade 22 protruding over this front end 21 and having a helical cutting edge 23 which extends rearwards from a tip 24 towards two opposite sides of the blade carrier 20 (FIG. 5). The cutting edge 23 engages a corresponding guide 25 in the inner wall of the end cap 7. This guide 25 is formed by a helical groove in the inner wall of the end cap 7. When advanced by the push rod 6, an additional rotational movement about the longitudinal axis of the tubular housing 2 is thereby imparted to the blade carrier 20.

In a retracted protected position of the blade carrier 20, it lies with its rear edge 26 protruding radially over the circumference of the push rod 6 against the projection 17 of the interior 9, whereby the furthermost retracted position of the blade carrier 20 is defined. Starting from this position, the blade carrier 20 can be pushed forwards by the push rod 6 into a cutting position and beyond that. In all cases, the front area of the blade 22 protrudes over the end cap 7 of the tubular housing 2.

A protective cap 27 engages over the front area of the blade carrier 20 carrying the blade 22. The protective cap 27 is arranged between the end cap 7 and the blade carrier 20 and surrounds the latter on all sides. The protective cap 27 is closed at its front end 28 and tapers towards this front end 28. It has a helical slit 29 whose contour corresponds to the helical cutting edge 23 which extends through this slit 29. Owing to this slit 29 and the cutting edge 23, which is guided in the guide 25 of the end cap 7 and projects through the slit 29, a rotation corresponding to the helical configuration of the cutting edge 23 is also imparted to the protective cap 27 when longitudinally displaced.

The protective cap 27 carries at its rear end a ring flange-shaped widening 30, which in the transition to the front, cylindrical area 31 engaging over the blade 22 forms a ring step 32, and which at its rear edge 33 carries a plurality of teeth 34 uniformly distributed over the circumference and pointing in the direction towards the rear end 3 of the housing 2. The protective cap 27 is mounted so as to be freely rotatable and displaceable in the longitudinal direction in both its front area 31 and the area of the widening 30 in a ring-shaped intermediate space between the blade carrier 20 and the end cap 7. It thereby surrounds the blade carrier 20 concentrically.

Figure 9:
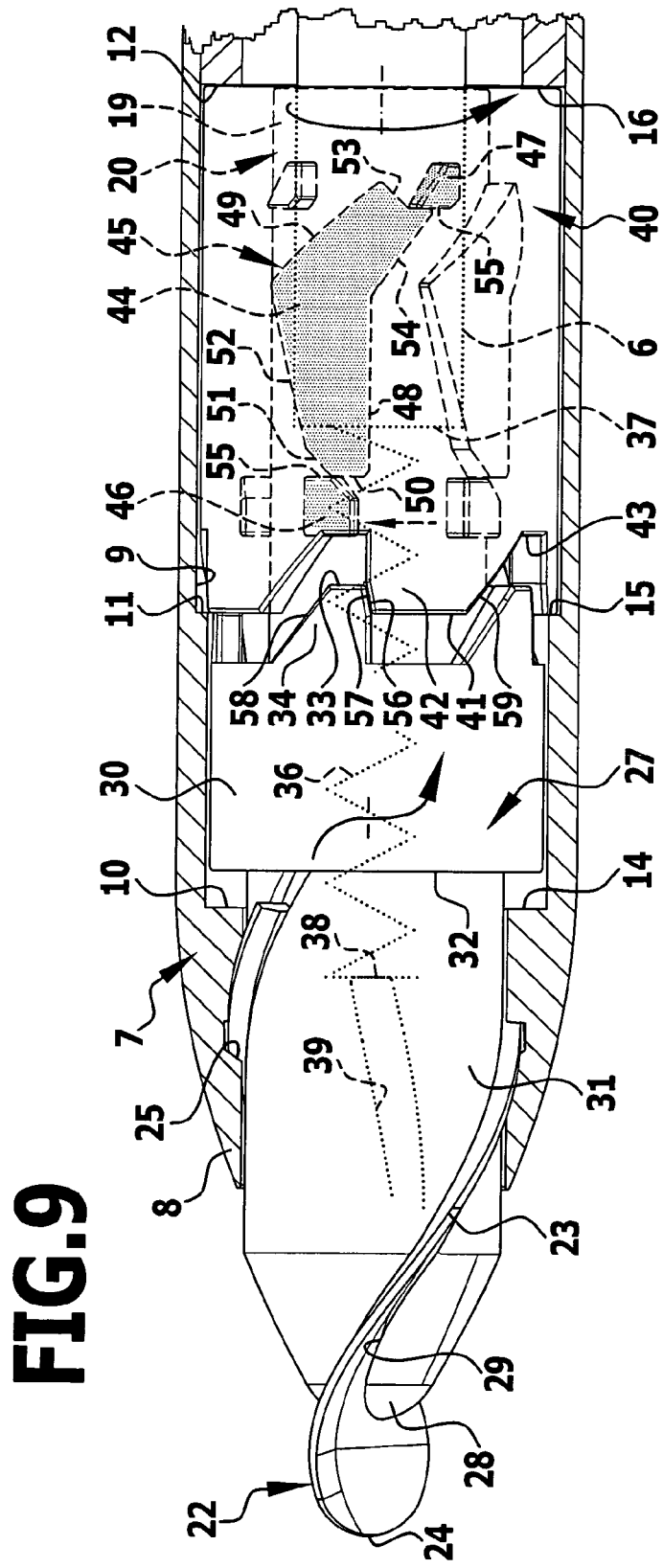
FIG. 9 a view, similar to FIG. 8, with the blade carrier during the transition from the blocked position to the cutting position.
Figure 10:
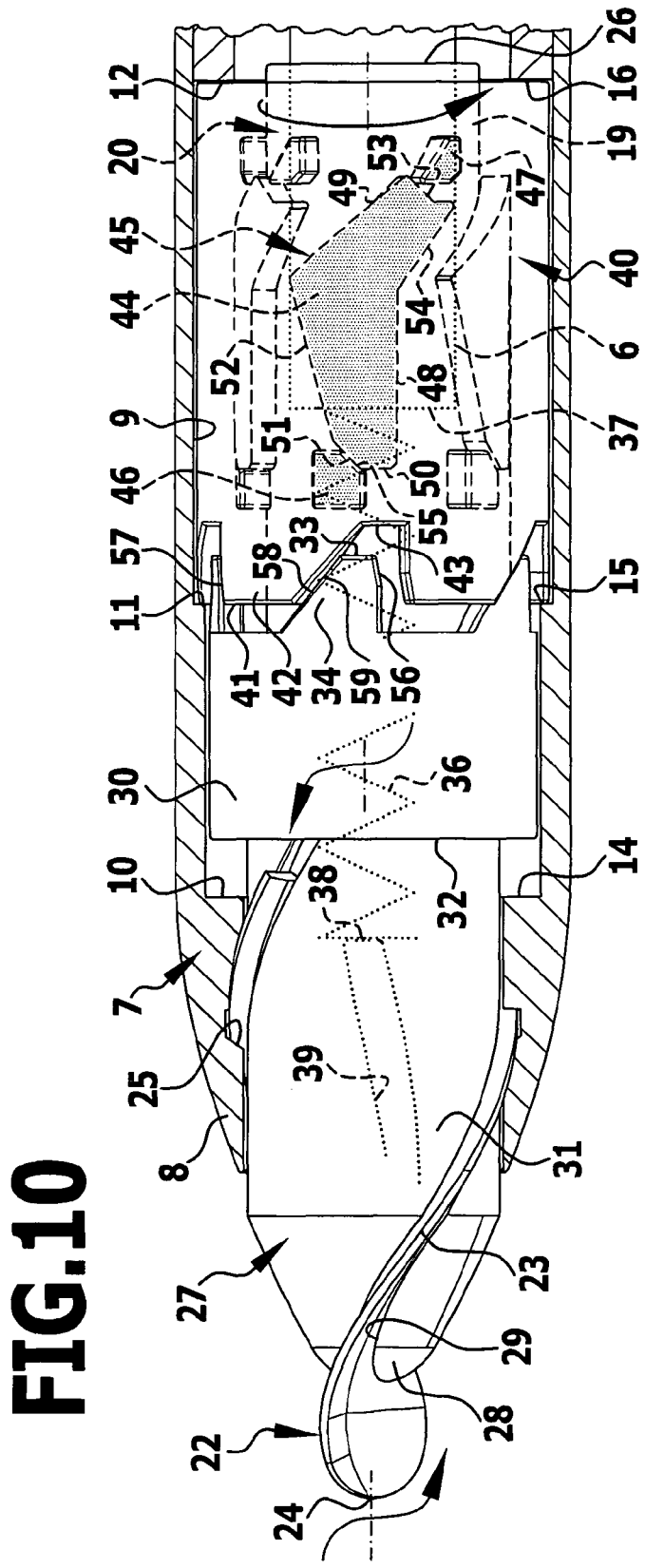
FIG. 10 a view, similar to FIG. 9, with the blade carrier in the cutting position and the protective cap in the work position.
Figure 11:
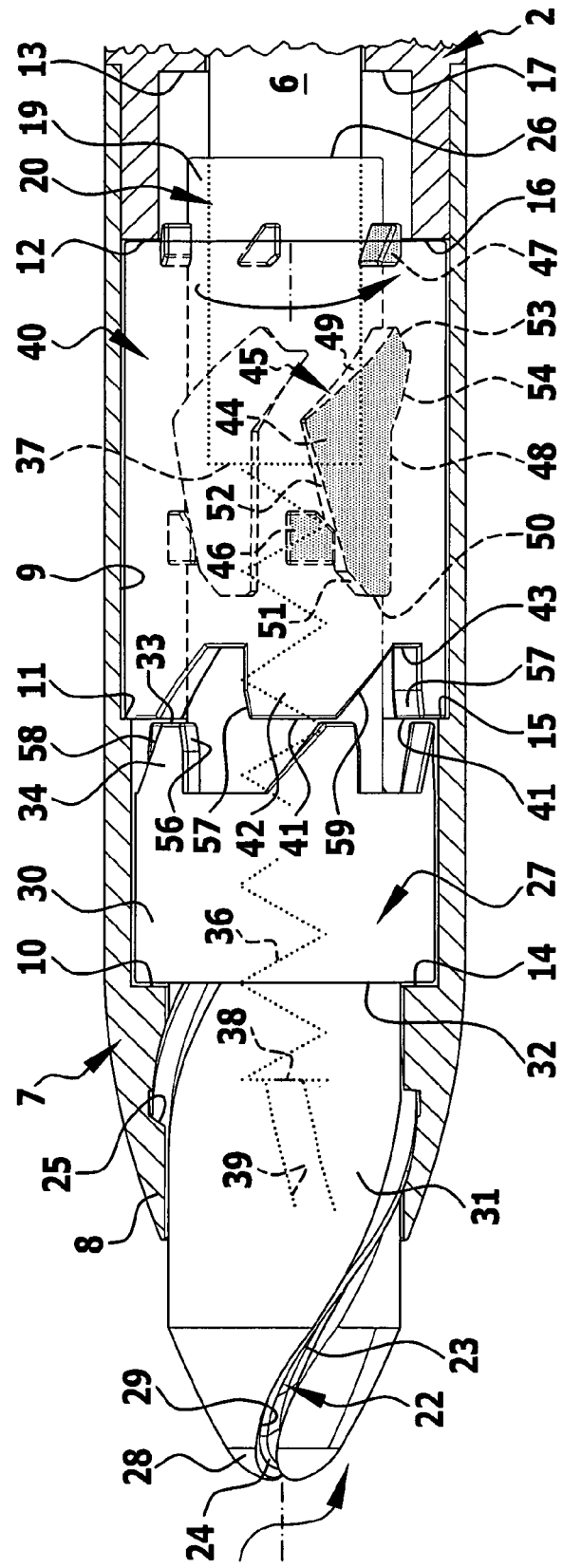
FIG. 11 a view, similar to FIG. 10, with the protective cap in the rest position and during the retracting movement of the blade carrier.

In an advanced rest position, the ring step 32 of the protective cap 27 abuts on the projection 14 of the end cap 7. Starting from this rest position, the protective cap 27 can be pulled back into the end cap 7 up to a retracted work position in which the teeth 34 ending in the rest position in front of the projection 15 project over this projection 15 (FIGS. 9 and 10). This displacement path is short and is limited to a portion of the depth of the teeth 34.

Arranged concentrically with the blade carrier 20 and the protective cap 27 in the interior 35 of the blade carrier 20 is a helical spring 36 which is supported, on the one hand, on the end face 37 of the push rod 6 and, on the other hand, on a projection 38, which is part of the protective cap 27 and projects through a slit-shaped opening 39 in the wall of the blade carrier 20 into its interior 35. By means of this helical spring 36 the protective cap 27 is displaced into its rest position and the blade carrier 20 into its protected position, i.e., the protective cap 27 abuts with its ring step 32 on the projection 14, and the blade carrier 20 with its rear edge 26 on the projection 17. Against the force of the helical spring 36, the blade carrier 20 can be displaced in the direction towards the cutting position, and a displacement of the protective cap 27 in the direction towards the work position is also possible.

A sleeve-shaped switching element 40 which concentrically surrounds the shaft 19 is mounted so as to be freely rotatable in a ring-shaped intermediate space between the shaft 19 of the blade carrier 20 and the inner wall of the end cap 7. The switching element 40 abuts on both the projection 15 and the projection 16 and is thereby mounted immovably in axial direction in the end cap 7. This switching element 40 carries at its front edge 41 facing the protective cap 27, opposite the teeth 34 of the protective cap 27, teeth 42 which are uniformly distributed over the circumference and are formed by indentations 43 extending from the edge 41.

Uniformly distributed over the circumference on the inner side of the switching element 40 are a plurality of island-shaped projections 44, whose outer edge forms a cam track 45 for cams 46, 47, which are arranged on the shaft 19 of the blade carrier 20 and protrude radially outwardly from it. The shaft 19 carries a plurality of first or front cams 46 distributed uniformly over the circumference and a plurality of second or rear cams 47 also distributed uniformly over the circumference, which are respectively located in a radial plane (FIG. 5). The terms 'first cam' and 'front cam' are herein used interchangeably, as are the terms 'rear cam' and 'second cam'. Upon displacement of the blade carrier 20 in the longitudinal direction, these cams 46 and 47 can rotate the switching element 40 by abutting on the cam tracks 45. The front and the rear cams successively abut on suitable sections of the cam track 45 and carry out the rotation in accordance with the shape and arrangement of these sections of the cam track 45.

In the embodiment shown, the cam track 45, closed within itself, comprises a first bottom section 48 extending parallel to the longitudinal direction of the housing 2, a third section 50 adjoining the front side of the island-shaped projection 44 and extending transversely to the longitudinal direction of the housing 2, adjoined by a fourth section 51 inclined rearwards at approximately 45° to the longitudinal axis of the housing 2, adjoined by a fifth section 52 inclined to a less pronounced extent in relation to the longitudinal direction of the housing 2, and a second section 49 inclined from the end of the fifth section 52 in the opposite direction at approximately 45° relative to the longitudinal axis of the housing 2. Adjoining the rear end of the second section 49 is a sixth section 53 with an upper portion extending forwards at approximately a right angle from the end of the second section 49, and a bottom portion arranged transversely to the longitudinal direction of the housing 2, and the bottom end of the sixth section 53 is joined by a seventh section 54 to the rear end of the first section 48. All sections of the embodiment shown are of straight-lined configuration.

The cams 46 and 47 are of such shape that at the sides at which they abut on different sections of the cam track 45, they have abutment surfaces 55 respectively extending parallel to these sections, i.e., in this way, the outer contour of the cams results, on the one hand, from the orientation of the sections 48 to 54 and, on the other hand, from the abutment or non-abutment of the respective cam on the cam track in the area of corresponding sections. Since front and rear cams are provided, not every cam necessarily abuts on all sections of the cam track, but the abutment is assumed by the front and rear cams one after the other.

Regarding operation of the described assembly, reference is made hereinbelow, in particular, to the representations of FIGS. 6 to 14. Before actuation, the entire assembly is in an initial position shown in FIG. 6, in which the protective cap 27 is in its advanced rest position, and the blade carrier 20 is in its retracted protected position. The teeth 34 of the protective cap 27 are disengaged from the teeth 42 of the sleeve-shaped switching element 40. In that area in which the protective cap 27 protrudes over the end cap 7, the cutting edge 23 of the blade 22 is completely retracted into the interior of the protective cap 27, so that the cutting edge 23 outside of the end cap 7 does not protrude over the protective cap 27. However, the cutting edge 23 in the portion of the protective cap 27 that is arranged in the interior of the end cap 7 still extends through the slit 29 of the protective cap 27 into the guide 25 in the inner wall of the end cap 7. In this position, the blade carrier 20 and the protective cap 27 are held by the helical spring 36, which pushes these two parts apart.

In this initial position, the front cams 46 respectively abut on the rear end of the first section 48 of the cam track 45, the rear cams 47 are retracted rearwards in relation to the cam tracks 45 and are not in contact with these.

To use the obturator, it is first necessary to activate the blade. This is done by pressing the pushbutton 5 and, consequently, advancing the push rod 6 and the blade carrier 20 fixedly connected to it. The blade carrier 20 is advanced against the action of the helical spring 36 and owing to the guidance of the helical cutting edge 23 in the guide 25 also slightly rotated. The front cam 46 thereby moves on a path extending at an incline to the longitudinal direction of the housing 2. In FIGS. 6 and 14, this path is indicated by arrow B. During this displacement, the front cams 46 respectively slide along the first section 48 of the cam track 45 and rotate the sleeve-shaped switching element 40 in the direction of arrows C in FIGS. 7 and 12 in a first direction. The cam track 45 is thus displaced upwards during this rotation in the representation of FIGS. 7 and 12.

Figure 12:
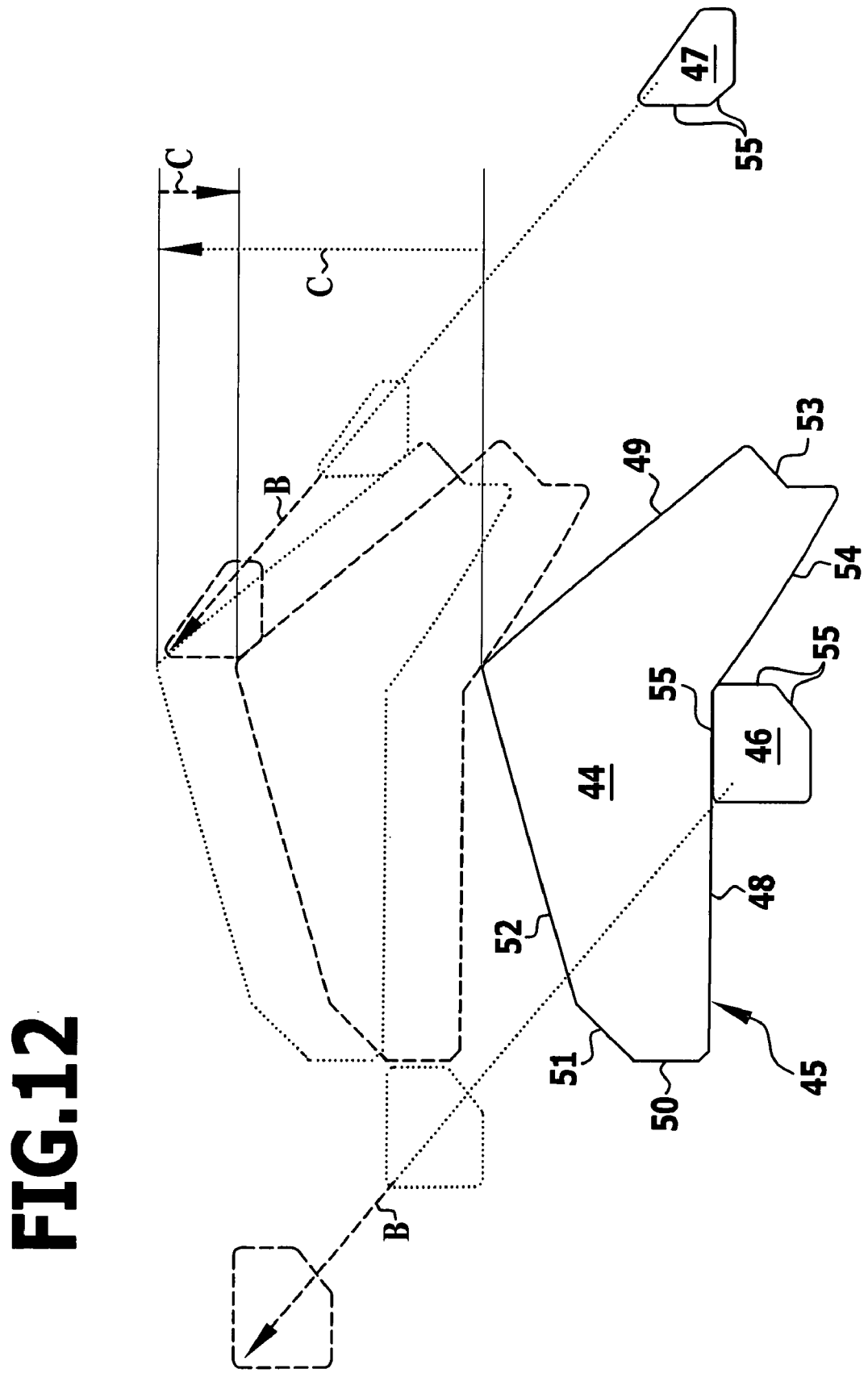
FIG. 12 a diagrammatic representation of the cam guide between blade carrier and switching element during the advancing movement of the blade carrier from the protected position in the direction towards the cutting position and up to an end position going beyond the cutting position.

During the advancing movement of the blade carrier 20, the front cams 46 move from the rear end of the first section 48 (solid contour in FIG. 12) to the front end of the first section 48 (dotted contour in FIG. 12), and they are then displaced even further forwards into an end position (dashed contour in FIG. 12). This further displacement takes place without the front cams 46 abutting on the cam track 45, i.e., the front cams 46 rotate the switching element 40 only during their abutment on the first section 48.

The arrangement of the front cams 46 and the rear cams 47 is selected such that the rear cams 47 abut on the second section 49 once the front cams 46 have left the first section 48. The rear cams 47 are also displaced on a path extending at an incline to the longitudinal axis and also corresponding to the direction of arrows B. Since the second section 49 extends at a steeper incline in relation to the longitudinal direction of the housing 2 than this direction of movement of the rear cams 47, indicated by arrow B, the rear cams 47 abut on the second section 49 and, upon further displacement of the blade carrier 20, rotate the switching element 40 in opposition to the first direction in a second direction, which is also indicated by arrow C in FIG. 12.

Figure 8:
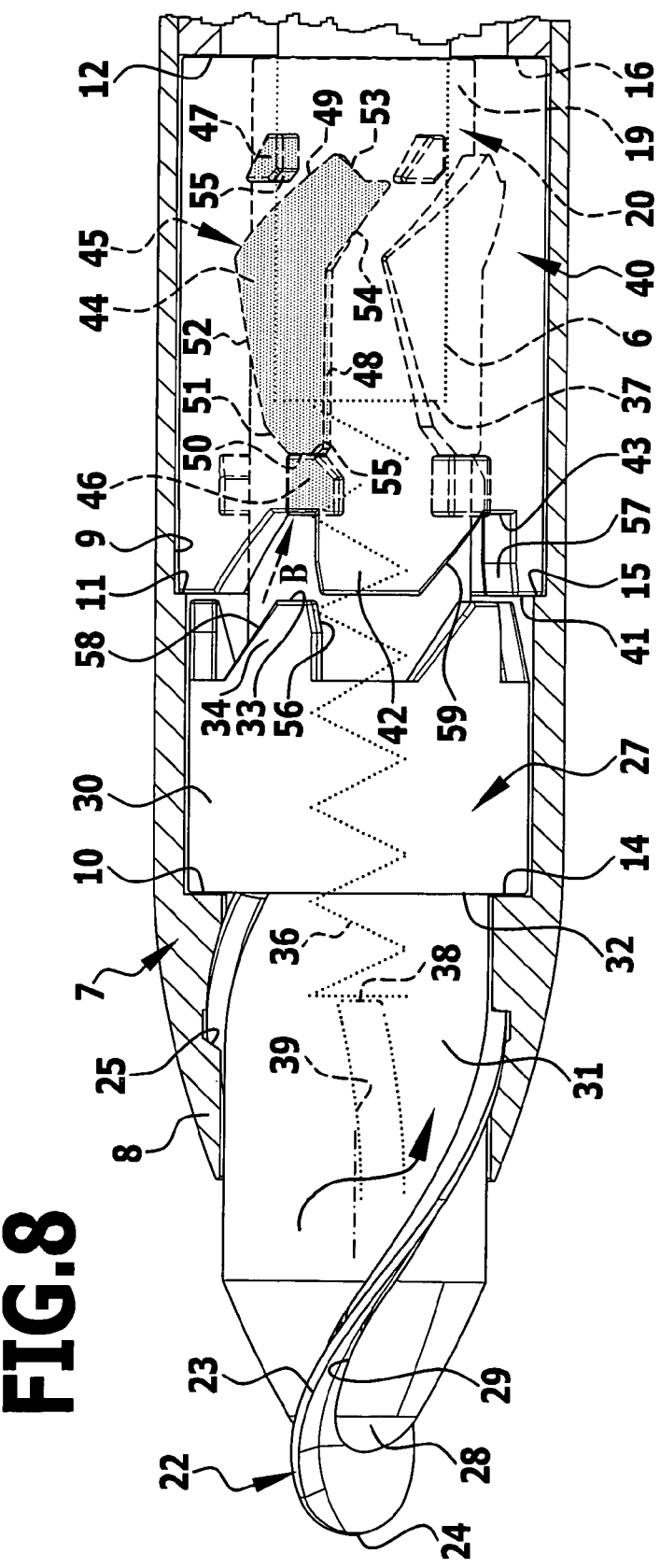
FIG. 8 a view, similar to FIG. 7, with the blade carrier and the switching element in the blocking position.
Figure 13:
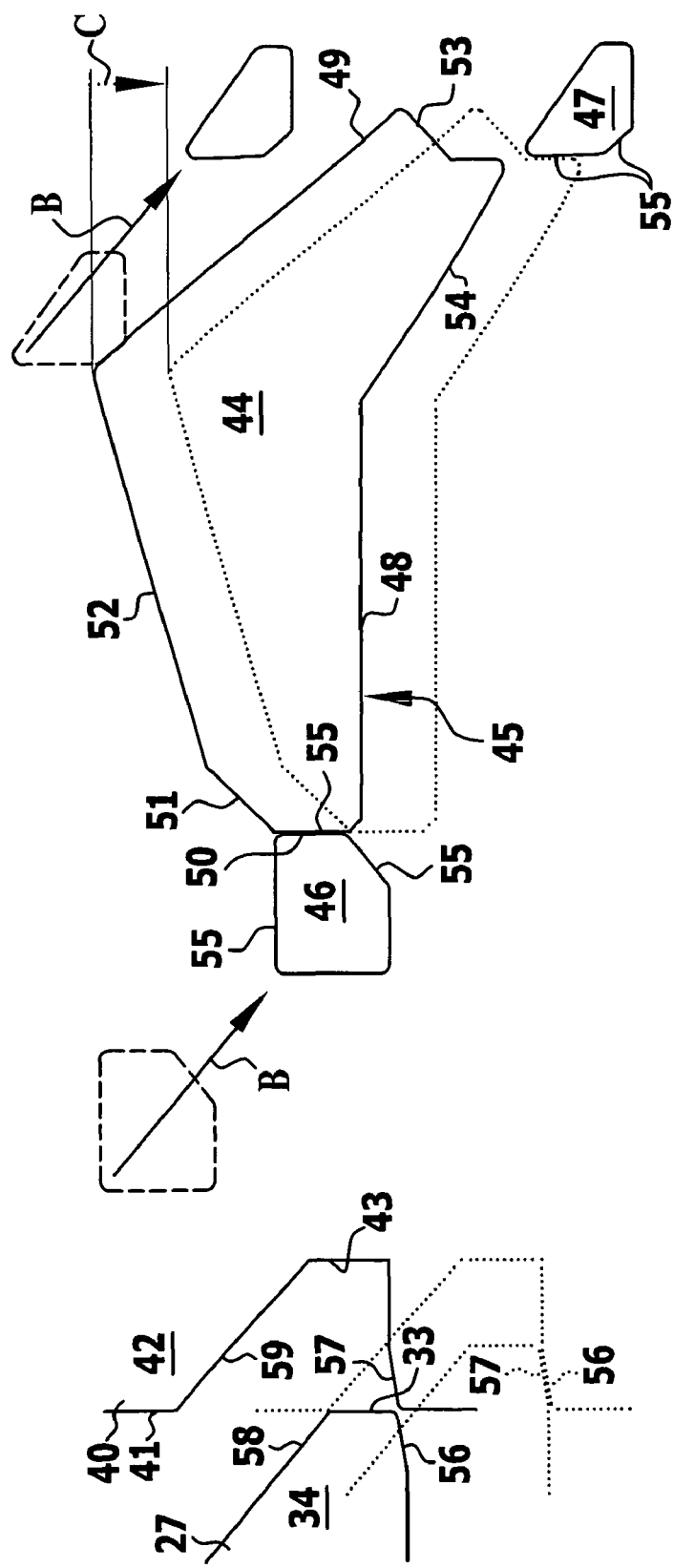
FIG. 13 a view of the cam guide between switching element and blade carrier and between switching element and protective cap during the displacement of the blade carrier from the end position into a blocking position and subsequently in the direction of the cutting position.

The advancing movement of the blade carrier 20 is delimited by a stop, not shown in the drawings. For example, this stop may be provided on the pushbutton 5. When the user releases the pushbutton again, after this foremost point has been reached, the blade carrier 20 is pushed back under the action of the helical spring 36, more particularly, on the same path indicated by arrow B. The front cams 46 then strike the third section of the cam track 45 as the cam track has been rotated in the second direction by the rear cam 47 and now lies with the third section 50 in the displacement path of the front cams 46 (FIG. 13). The rearward movement of the blade carrier 20 is thus blocked by the abutment of the front cams 46 on the third section 50 of the cam track 45. In this blocked position, the cutting edge 23 protrudes over the entire area of the slit 29 from the protective cap 27, as shown in FIG. 8. In this blocked position, the obturator is ready to be used to pierce a body wall (solid contour in FIG. 13).

During the piercing, the surgeon places the tip 24 of the blade 22 on the body wall and advances the obturator, while at the same time rotating it, in the direction towards the body wall, so that the blade 22 penetrates the body wall along the cutting edge 23. During this penetration, the front end 28 of the protective cap 27 abuts on the body wall and is pushed by it against the action of the helical spring 36, while at the same time being rotated by the guidance of the helical cutting edge 23, into the end cap 7 (FIGS. 9 and 13). The teeth 34 of the protective cap 27 thereby move in between the teeth 42 of the switching element 40 and abut on one another with a very steep flank 56 and 57, respectively, which is only slightly inclined in relation to the longitudinal direction of the housing 2. This causes the switching element 40 to be rotated in the second direction, so that the front cams 46 of the blade carrier 20 are thereby advanced beyond the end of the third section 50 (dotted contour in FIG. 13 and solid contour in FIG. 14). The front cams 46 thus reach the start of the fourth section 51 extending rearwards at an incline. This results in a slight rearward movement of the blade carrier 20 and in a further rotation of the switching element 40 in the second direction (dotted contour in FIG. 14).

However, both this rearward movement of the blade carrier 20 and the rotation of the switching element 40 are very slight since during the rotation of the switching element 40 the opposite flanks 58 and 59, respectively, of the teeth 34 and 42 enter into abutment and prevent any further rotational movement of the switching element 40 (FIGS. 10 and 14). In this position, the blade carrier 20 is prevented from being displaced rearwards any further as the front cams 46 are supported on the fourth section 51 of the cam track 45 (dotted position in FIG. 14). This position is referred to as cutting position of the blade carrier 20. In this cutting position, the cutting edge 23 continues to protrude over the protective cap 27 which, for its part, is in the retracted work position. The surgeon can, therefore, continue with the piercing of the body wall until it has been completely pierced.

This results, upon advancing the obturator 1 further, in the protective cap 27 also passing with its tapering front end 28 and the adjoining cylindrical area 31 through the opening made in the body wall and now no longer being pushed sufficiently strongly against the action of the helical spring 36 into the end cap 7. The protective cap 27 can now be displaced forwards again under the action of the helical spring 36 into its rest position until the ring step 32 of the shaft-shaped widening 30 abuts on the projection 14. The teeth 34 of the protective cap 27 are thereby disengaged from the teeth 42, i.e., the switching element 40 is released and can now rotate freely again. Therefore, under the action of the helical spring 36, the blade carrier 20 is now retracted into its protected position as the switching element 40 no longer blocks this rearward movement. The switching element 40 is simultaneously rotated in the second direction as the front cams 46 slide along the fifth section 52 (dashed contour in FIG. 14) until the initial position shown in FIG. 6 is reached again, in which the blade carrier 20 is completely retracted and in which the cutting edge 23 in the portion lying outside the end cap 7 is completely covered by the protective cap 27.

A full work cycle has thus been completed and can be repeated in the same way.

It will be clear from the representation of FIG. 14 that the rear cams 47 are located opposite the sixth section 53 of the cam track 45 when the blade carrier 20 moves from the blocked position to the cutting position (dotted contour in FIG. 13 and solid and dotted contours in FIG. 14). An advancing of the blade carrier 20 in the direction towards the end position, i.e., beyond the blocked or cutting position, is thereby prevented. This is a safeguard in the event that the surgeon should inadvertently actuate the pushbutton 5 during the cutting operation. This actuation does not result in any displacement of the blade carrier 20 as it is secured against axial displacement in both directions, more particularly, by the front cams 46 and rear cams 47 abutting on opposite sides on the cam track 45.

The construction of the described assembly is very simple as only three movable parts and a helical spring have to be used in the tubular housing. Assembly is also very simple as it is sufficient to concentrically assemble these parts and then connect the end cap firmly to the adjoining shaft-shaped part of the tubular housing. Separation and then cleaning may also be carried out in the same way.

The entire assembly can be accommodated in the front part of the tubular housing near the blade without its outer diameter having to be increased and, therefore, with the exception of the pushbutton 5, no parts of the retracting device need be arranged in the grip area of the obturator 1.

The invention claimed is:

1. Surgical obturator for piercing a body wall, comprising:
   a tubular housing,
   a blade carrier displaceable in the tubular housing in a longitudinal direction between an advanced cutting position and a retracted protected position,
   a blade with a cutting edge held on the blade carrier, the cutting edge being guided in a correspondingly extending guide of the tubular housing,
   a protective cap engaging over the blade and being displaceable in the tubular housing in the longitudinal direction between an advanced rest position in which the blade is completely covered in the protected position and a retracted work position, the protective cap having a slit through which the cutting edge of the blade passes and, in the work position of the protective cap, the blade projects through the slit, and
   a retracting device arranged in the tubular housing and displacing the blade from the cutting position to the protected position, the retracting device being activatable by displacement of the protective cap from the work position to the rest position, the retracting device comprising a switching element which fixes the blade in the cutting position and, upon activation, releases the blade for displacement to the rest position, the switching element being mounted in the tubular housing so as to be freely rotatable about a longitudinal axis of the tubular housing and immovable in the longitudinal direction, and the switching element being rotatable, upon displacement of at least one of the blade carrier and the protective cap in the longitudinal direction, by means of a cam guide which is operative between the switching element, on the one hand, and at least one of the blade carrier and the protective cap, on the other hand;
   wherein:

the switching element is a sleeve which concentrically surrounds the blade carrier;

the cam guide operative between the switching element and the blade carrier is formed by cam tracks and cams adapted to abut thereon, the cams and the cam tracks being arranged on an outer side of the blade carrier and on an inner wall of the switching element, respectively; and a first cam, upon displacement of the blade carrier from the protected position in the longitudinal direction towards the cutting position, slides along a first section of a corresponding cam track that extends at an incline to the direction of displacement of the blade carrier and thereby rotates the switching element from an initial position in a first direction, and a second cam enters into abutment with a second section of the corresponding cam track extending in an opposite direction at an incline to the direction of displacement of the blade carrier once the first cam has moved past the first section of the cam track, so that the switching element is rotated in an opposite second direction into a blocking position in which, upon subsequent retraction of the blade carrier from an end position located in front of the cutting position, a portion of the blade carrier strikes a portion of the switching element and thereby prevents any further retraction of the blade carrier.

2. Surgical obturator in accordance with claim 1, wherein the protective cap is acted upon by a spring which displaces the protective cap from the work position to the rest position.

3. Surgical obturator in accordance with claim 1, wherein the blade carrier is acted upon by a spring which displaces the blade carrier from the cutting position to the protected position.

4. Surgical obturator in accordance with claim 1, wherein the protective cap and the blade carrier are acted upon by a common spring which pushes the protective cap and the blade carrier apart, the spring displacing the protective cap from the work position to the rest position and the blade carrier from the cutting position to the protected position.

5. Surgical obturator in accordance with claim 4, wherein the spring is a helical spring which is arranged in an interior of the blade carrier and is supported at one end on a projection of the protective cap that extends through a wall of the blade carrier into the interior thereof.

6. Surgical obturator in accordance with claim 1, wherein the cutting edge of the blade is of helical configuration, so that the blade carrier, upon displacement in the longitudinal direction relative to the tubular housing, and the protective cap, upon longitudinal displacement relative to the blade carrier, are rotated relative to each other about a longitudinal axis of the blade carrier.

7. Surgical obturator in accordance with claim 1, wherein the blade carrier comprises a cylindrical shaft which is arranged concentrically with the tubular housing.

8. Surgical obturator in accordance with claim 1, wherein the blade carrier is connected to a push rod which extends through the tubular housing as far as a push device at an end of the tubular housing remote from the blade.

9. Surgical obturator in accordance with claim 1, wherein a plurality of similar cam tracks and cams are arranged along a circumference of the blade carrier and the switching element such that in successive work cycles the cams respectively abut on an adjacent cam track.

10. Surgical obturator in accordance with claim 1, wherein each cam track has associated with it two cams which, upon displacement of the blade carrier relative to the switching element, abut one after the other on the cam track.

11. Surgical obturator in accordance with claim 1, wherein the cam tracks are formed by an edge of an island-shaped projection.

12. Surgical obturator in accordance with claim 1, wherein the portion of the blade carrier that strikes the portion of the switching element to prevent further retraction is formed by the first cam.

13. Surgical obturator in accordance with claim 1, wherein the portion of the switching element struck by the portion of the blade carrier is formed by a third section of the cam track that extends transversely to the longitudinal direction of the tubular housing.

14. Surgical obturator in accordance with claim 1, wherein the cam track and the cams between the switching element and the protective cap are formed by side flanks of teeth which are arranged on end faces of the protective cap and the switching element that face one another, and which are in engagement when the protective cap is retracted into the work position.

15. Surgical obturator in accordance with claim 14, wherein the flanks of the teeth are so arranged and designed that the teeth of the protective cap, upon retraction of the protective cap from the rest position to the work position, rotate the switching element from the blocking position in the first direction until the stop of the blade carrier reaches a fourth section of the corresponding cam track of the switching element, which extends at an incline to the longitudinal direction of the tubular housing and adjoins the stop of the switching element.

16. Surgical obturator in accordance with claim 15, wherein the flanks of the teeth are so designed that a rotation of the switching element in the second direction under the influence of the stop of the blade carrier abutting on the fourth section is limited such that the blade carrier, in relation to its position with the two stops abutting on each other, is retracted only slightly as far as the cutting position.

17. Surgical obturator in accordance with claim 16, wherein the engagement of the teeth of the blade carrier and the protective cap is released upon displacement of the protective cap into the rest position, so that the limitation of the rotatability of the switching element is eliminated.

18. Surgical obturator in accordance with claim 17, wherein the corresponding cam track has a fifth section which adjoins the inclined fourth section and along which the first cam of the blade carrier slides upon retraction of the blade carrier from the cutting position to the protected position and thereby rotates the switching element in the second direction into the initial position for the next work cycle.

19. Surgical obturator in accordance with claim 1, wherein when the switching element is located in the blocking position and the stop of the blade carrier is in abutment with the fourth section, the second cam of the blade carrier is located opposite a sixth section of the corresponding cam track, which prevents a displacement of the blade carrier in the direction from the protected position to the cutting position.

* * * * *